(12) United States Patent
Kraus

(10) Patent No.: US 8,629,312 B2
(45) Date of Patent: Jan. 14, 2014

(54) METHOD FOR PRODUCING OLEFINS

(75) Inventor: George A. Kraus, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 13/639,209

(22) PCT Filed: Mar. 16, 2011

(86) PCT No.: PCT/US2011/028672
§ 371 (c)(1),
(2), (4) Date: Dec. 18, 2012

(87) PCT Pub. No.: WO2011/126688
PCT Pub. Date: Oct. 13, 2011

(65) Prior Publication Data
US 2013/0102823 A1 Apr. 25, 2013

Related U.S. Application Data

(60) Provisional application No. 61/321,721, filed on Apr. 7, 2010.

(51) Int. Cl.
*C07C 1/00* (2006.01)

(52) U.S. Cl.
USPC ........... 585/638; 585/324; 502/208; 502/213; 502/326; 502/339

(58) Field of Classification Search
USPC .......... 585/324, 368; 502/208, 213, 325, 324, 502/333, 339
See application file for complete search history.

(56) References Cited

U.S. PATENT DOCUMENTS 5,077,447 A * 12/1991 Miller et al. .................. 585/638

FOREIGN PATENT DOCUMENTS

| WO | WO-9206059 A1 | 4/1992 |
| WO | WO-9206059 A1 | 4/1992 |
| WO | WO-2011126688 A1 | 10/2011 |
| WO | WO-2011126688 A1 | 10/2011 |

OTHER PUBLICATIONS

Goosen et al. A Mild and Efficiento Protocol for the Conversion of Carboxylic Acids to Olefins by a Catalytic Decarbonylative Elimination Reaction. ChemComm. 2004, pp. 724-725.*

Yamamoto, A. Toward Development of Environmentally Benign Processes Catalyzed by Transition-Metal Complexes. Pure Appl. Chem., vol. 74, No. 1, 2002. pp. 2-3.*

"Stearic acid." Encyclopaedia Britannica. Encyclopaedia Britannica Online Academic Edition. Encyclopaedia Britannica Inc., 2013. <http://www.britannica.com/EBchecked/topic/564584/stearic-acid>>.*

"International Application Serial No. PCT/US2011/028672, Written Opinion mailed May 23, 2011", 10 Pgs.

Goosen, L., at al., "A mild and efficient protocol for the conversion of carboxylic acids to olefins by a catalytic decarbonylative elimination reaction", Chemical Communications, 724(6), (2004), 724-725.

Miller, Joseph A., et al., "A highly catalytic and selective conversion of carboxylic acids to 1-alkenes of one less carbon atom", J. Org. Chem, 58(1), (1993), 18-20.

Miyaura, N. et al., "Palldium Catalyzed reation of 1-alkenylboronates with vinylic halides", Organic Syntheses, 68, XP002636757, paragraph [02.8], (1993), 532.

Tanaka, E. T, at al., "Synthesis of 1-Nonene from Decanoic Acid by Polymer-Bound Palladium Complexes", Chemistry Letters, Chemical Society of Japan, vol. 12, XP008136396 ISSN: 0366-7022 p. 1277, col. 1, paragraph 5, col. 2, last paragraph figures 1,3, (1997), 1277-1278.

"International Application Serial No. PCT/US2011/028672, Search Report mailed May 23, 2011", 4 Pgs.

"International Application Serial No. PCT/US2011/028672. Written Opinion mailed May 23, 2011", 10 Pgs.

"International Application Serial No. PCT/US2011/028672, Written Opinion mialed Apr. 26, 2012", 8 pgs.

Miller, Joseph A., et al., "A highly catalytic and selective conversion of carboxylic acids to 1-alkenes of one less carbon atom", J. Org. Chem., 58(1), (1993), 18-20.

Miyaura, N, et al., "Palldium Catalyzed reaction of 1-alkenylboronates with vinylic halides", Organic Syntheses, 68, XP002636757, paragraph [02.8], (1993), 532.

Tanaka, E. T, et al., "Synthesis of 1-Nonene from Decanoic Acid by Polymer-Bound Palladium Complexes", Chemistry Letters, Chemical Society of Japan, vol. 12, XP008136396 ISSN: 0366-7022 p. 1277, col. 1, paragraph 5, col. 2, last paragraph figures 1,3,(1997), 1277-1278.

Zapf, A., "Novel substrates for palladium-catalyzed coupling reactions of arenes", Angew Chem Int Ed Engl., 42(44), (Nov. 17, 2003), 5394-9.

* cited by examiner

*Primary Examiner* — Walter D Griffin
*Assistant Examiner* — Jelitza Perez
(74) *Attorney, Agent, or Firm* — Schwegman Lundberg & Woessner, P.A.

(57) ABSTRACT

The present invention provides a method to produce olefins by the decarboxylation of organic carboxylic acids in the presence of an organopalladium catalyst.

6 Claims, No Drawings

METHOD FOR PRODUCING OLEFINS

CROSS REFERENCE TO RELATED APPLICATION

This application is a nationalization under 35 U.S.C. 371 of PCT/US2011/028672, filed 16 Mar. 2011 and published as WO 2011/126688 on 13 Oct. 2011, claims priority to U.S. provisional application Ser. No. 61/321,721 filed Apr. 7, 2010, which applications are incorporated by reference herein in their entirety.

GOVERNMENT GRANT SUPPORT

This invention was made with government support under Grant No. NSF EEC0813570 awarded by the National Science Foundation. The government has certain rights in the invention.

BACKGROUND OF THE INVENTION

Alpha-olefins have many uses. For example they are used to prepare polyethylene, polypropylene, and many or other polymeric plastic materials having a wide variety of uses. They are also useful in preparing many specialty chemicals. Typically alpha-olefins are produced from petroleum feed stocks. Alpha-olefins have an estimated market of at least 2.5 million tons per year.

Recently, L. J. Groor3en et al., *Chem. Commun.*, 727 (2004) reported the decarboxylation of aliphatic carboxylic acids to yield α-olefins using the catalyst bis(2-diphenylphosphenophenyl)ether plus $PdCl_2$ in polar solvents such as 1,3-dimethyltetrahydro-2(1H)-pyrimidinone in the presence of pivalic anhydride, at 110° C. In contrast to this complex system, J. A. Miller et al., *J. Org. Chem.*, 58, 18 (1993) reported the conversion of ($C_{10}$-$C_{12}$)alkanoic acids in the presence of acetic anhydride or their symmetrical anhydrides, to the corresponding ($C_{n-1}$)1-alkenes at 250° C. in the presence of $(Ph_3)P_2Pd(Cl_2)$ with added $Ph_3P$. At 250° C., 40 Torr, stearic acid and myristic acid were converted to 1-heptadecene and 1-tridecene at 250° C. Miller et al. also reported that the use of $(Ph_3P)_4Pd$ plus $Ph_3P$ was much less efficient in the conversion of decanoic acid to 1-nonene in the presence of $Ac_2O$, than was $(Ph_3)PdCl_2$ with added $Ph_3P$.

However, there is a continuing need for methods to effectively convert a wide variety of organic carboxylic acids to the corresponding terminal and internal olefins, employing a variety of feed stocks. For example, there is a continuing need to find new non-petroleum based feed stocks from which they can be made, such as those generated from renewable resource feed stocks.

To improve the economic outlook of biodiesel and alkyl esters in general, the feedstock selection becomes critical. In particular, feeds containing high free fatty acid content, such as found in beef tallow or yellow grease, are significantly less expensive than vegetable oils, such as soybean, flaxseed or rapeseed oil. F. Ma et al., *Ind. Eng. Chem.*, 37, 3768 (1998). These high free fatty acid feedstocks present significant processing problems in standard biodiesel manufacture since the free fatty acid is saponified by the homogeneous alkali catalyst that is used to transesterify triglycerides leading to a loss of catalyst as well as increased purification costs. See, e.g., D. G. B. Boocock et al., *J. Amer. Oil. Chem. Soc.*, 75 1167 (1998).

SUMMARY OF THE INVENTION

The present invention provides a catalytic method for the decarboxylation of an organic carboxylic acid or mixtures thereof, comprising:

a) reacting an organic carboxylic acid of the formula (I):

R—CH(Y)—CH(Z)—CO$_2$H    (I)

wherein each of R, Y and Z is individually H or an organic group, with the proviso that at least one on R, Y or Z is an organic group or R is H and Y and Z taken together are a divalent organic group, with an anhydride of the general formula $R^1C(O)OC(O)R^1$ wherein $R^1$ is ($C_1$-$C_6$)alkyl, preferably ($C_1$-$C_4$)alkyl to yield a reaction mixture comprising a mixed anhydride of the formula (II):

$R^1$—C(O)—O—C(O)—CH(Z)—CH(Y)R (II);

b) reacting the mixed anhydride with a catalytic amount of $Pd(PPh_3)_4$ in the reaction mixture to yield an intermediate (III) of the formula $R^1$—C(O)—O—Pd)PPh$_3$)$_2$—C(O)CH(Z)—CH(Y)R
   (III); and c) decomposing intermediate (III) to yield a compound of formula R—C(Y)=C(Z) (IV) and $P(Ph_3)_4$, wherein steps (a)-(c) are carried out in the absence of a solvent.

Preferably, the method is carried out at a temperature above about 190° C., e.g., at about 195-250° C. The method can be carried out at atmospheric pressure but, in the case of higher molecular weight reactants and products, is preferably carried out at less than 1 atm pressure, e.g., at about 10-30 Torr. The temperature can be selected so that compound of formula IV, and preferably the other reactants can be isolated by distillation from the reaction mixture.

Preferably, the effective catalytic amount of $Pd(PPh_3)_4$ is formed in situ by combining $PdCl_2$ with excess $PPh_3$ in the reaction mixture, so that the Pd(0) present in the $Pd(PPh_3)_4$ is about 0.01-0.1 mol-% of (I). Preferably, the combination provides about 0.01-0.1 mol-% Pd(0) of (I) and about 0.25-5.0 mol-% $PPh_3$ of (I) to the reaction mixture.

While acetic anhydride is suitable for use at lower temperatures and higher pressures, its volatility presents a problem at higher temperatures and/or low pressures. Therefore, a higher boiling anhydride, such as pivalic anhydride is useful under such operating conditions.

A wide variety of aliphatic, branched and aromatic carboxylic acids of formula I can be converted into alkenes by the present method. For example, saturated and unsaturated 1-alkanoic acids having from about 5-22 carbon atoms ("fatty acids") or about 6-18 carbon atoms, or about 7-12 carbon atoms can be converted into the corresponding 4-21, 5-17 or 6-11 carbon atom 1-alkenes. E.g., in formula I, Y and Z can be H and R can be ($C_2$-$C_{19}$)alkyl, ($C_3$-$C_{15}$)alkyl or ($C_4$-$C_9$)alkyl. Representative reactions of this class are shown in Scheme I, below.

Scheme I

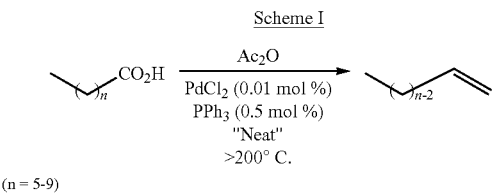

(n = 5-9)

In other embodiments of the invention, at least one of R, X or Y is aryl. In one embodiment of the invention, R is benzyl and the compound of formula IV is Ph-CH$_2$—CH=CH$_2$.

In other embodiments of the invention, cyclic carboxylic acids or dicarboxylic acids can be converted to cycloalkenes, such as when R is H and Z and Y taken together are —(CH$_2$)$_n$— wherein n is 3-5.

In other embodiments of the invention, at least one of R, Z and X is ($C_1$-$C_4$)alkyl. Other embodiments comprise the decarboxylation or bis(decarboxylation) of compounds of formula I wherein Z and Y are H and R is $XO_2C$—$(CH_2)_p$—, wherein X is H or ($C_1$-$C_4$)alkyl. p is 8-20, to yield 1,ω-dienes or 1-alkoxycarbonyl(alk-ω-enes). Representative reactions of this class are shown in Scheme II, below.

Scheme II

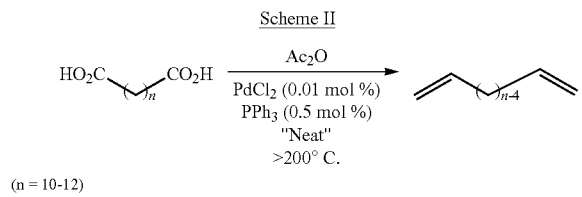

(n = 10-12)

Simple polymeric monomers can be readily prepared. For example, when R is $CO_2R^1$, Y is H and Z is H in formula I, IV is methylacrylate ($CH_2$=CH—$CO_2CH_3$).

The present method can be employed to remove free fatty acids from a variety of plant and animal feedstocks, so that the feedstocks can undergo further processing of the glycerides to yield the methyl and ethyl fatty acid esters that make up "biodiesel." Such oils and fats include soy oil, palm oil, flaxseed oil, rapeseed oil, and oils produced by algae, as well as animal fats and oil such as beef tallow or yellow grease.

DETAILED DESCRIPTION OF THE INVENTION

In compounds I, II, III, and IV, R, Y and Z can individually be organic groups or "radicals" that are substituted or unsubstituted, including alkyl, aryl, aralkyl cycloalkyl, cycloalkylalkyl, heterocyclyl, heterocyclylalkyl, heteroaryl, heteroarylalkyl or the like. R, Y and Z each can include about 1-20 carbon atoms, and/or can include double or triple bonds. R, Y and Z can also include heteroatoms. One or two of R, Y and Z can be H. Also, Y and Z together can be a divalent organic group such as -(alkyl)-, e.g., —$(CH_2)_n$—, wherein x is 3-5.

R, Y and Z can each be substituted or unsubstituted as those terms are defined herein. Substituted alkyl, alkenyl, alkynyl, cycloalkyl, cycloalkylalkyl, cycloalkenyl, and cycloalkenylalkyl groups as well as other substituted groups also include groups in which one or more bonds to a hydrogen atom are replaced by one or more bonds, including double or triple bonds to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

In general, "substituted" refers to an organic group as defined herein such as R, Y and Z in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Substituents must be selected so that they do not interfere with the catalytic activity of the Pd(0) catalyst or with its precursors.

Non-limiting examples of substituents that can be bonded to a substituted carbon (or other) atom include halo (F, Cl, Br, I), OR', e.g., alkoxy, $OC(O)N(R')_2$, CN, NO, $NO_2$, $ONO_2$, azido, haloalkyl, haloalkoxy, e.g., $OCF_3$, O (oxo), S (thiono), C(O), S(O), methylenedioxy, ethylenedioxy, $N(R')_2$, SR', SOR', $SO_2R'$, $SO_2N(R')_2$, $SO_3R'$, C(O)R', C(O)C(O)R', C(O)$CH_2$C(O)R', C(S)R', C(O)OR', OC(O)R', C(O)N(R')_2$, OC(O)N(R')_2$, C(S)N(R')_2$, $(CH_2)_{0-2}$N(R')C(O)R', $(CH_2)_{0-2}$N(R')N(R')_2$, N(R')N(R')C(O)R', N(R')N(R')C(O)OR', N(R')N(R')CON(R')_2$, N(R')SO_2R'$, N(R')SO_2N(R')_2$, N(R')C(O)OR', N(R')C(O)R', N(R')C(S)R', N(R')C(O)N(R')_2$, N(R')C(S)N(R')_2$, N(COR')COR', N(OR')R', C(=NH)N(R')_2$, C(O)N(OR')R', or C(=NOR')R' wherein R' can be hydrogen or a carbon-based moiety such as benzyl or ($C_1$-$C_4$)alkyl, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

C(O) and S(O)_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)_2$ group is bound to one carbon and one nitrogen atom, the resulting unit is termed a "sulfonamide." When a S(O)_2$ group is bound to two nitrogen atoms, the resulting unit is termed a "sulfamate."

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

As to any of the R, Y and Z other groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

An "acyl" group ($R^1C(O)$) as the term is used herein refers to a group containing a carbonyl moiety wherein the group is bonded, to a moiety such as a pyrimidine ring, via the carbonyl carbon atom. The carbonyl carbon atom is also bonded to $R^1$. A nicotinoyl group (pyridyl-3-carbonyl) group is an example of an acyl group within the meaning herein. Other examples include acetyl, i-butyroyl, benzoyl, phenylacetyl, pyridylacetyl, cinnamoyl, and acryloyl groups and the like.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "($C_x$—$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "($C_x$—$C_y$)perfluoroalkylene," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkylene, more preferred is —($C_1$-$C_3$)perfluoroalkylene, most preferred is —$CF_2$—.

Alkyl groups include straight chain and branched alkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, halo, amino, hydroxy, cyano, carboxy, nitro, thio, alkoxy, and halogen groups.

Cycloalkyl groups are $C_3$-$C_{12}$ cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

Unless specifically indicated to the contrary, the cycloalkyl ring can be substituted with as many as n−1 substituents wherein n is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above.

(Cycloalkyl)alkyl groups, also denoted cycloalkylalkyl, are alkyl groups as defined herein in which a hydrogen or carbon bond of the alkyl group is replaced with a bond to a cycloalkyl group as defined above.

Alkenyl groups include straight and branched chain alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH($CH_3$), —CH═C($CH_3$)$_2$, —C($CH_3$)═$CH_2$, —C($CH_3$)═CH($CH_3$), —C($CH_2CH_3$)═$CH_2$, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7.

Cycloalkenyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$) among others.

The term "heteroalkyl" by itself or in combination with another term means, unless otherwise stated, a straight or branched chain alkyl group consisting of the stated number of carbon atoms and one or two heteroatoms selected from the group consisting of non-peroxide O, N(R), and S, and wherein the nitrogen and sulfur atoms may be optionally oxidized and the nitrogen heteroatom may be optionally quaternized. R can be H, alkyl, aryl, aralkyl or a suitable protecting group. The heteroatom(s) may be placed at any position of the heteroalkyl group, including between the rest of the heteroalkyl group and the fragment to which it is attached, as well as attached to the most distal carbon atom in the heteroalkyl group. Examples include: —$CH_2$—$CH_2CH_2$—OH, —$CH_2$—$CH_2$—NH—$CH_3$, —$CH_2$—S—$CH_2$—$CH_3$, —$CH_2CH_2$—S(=O)—$CH_3$, and —$CH_2CH_2$—O—$CH_2CH_2$—O—$CH_3$. Up to two heteroatoms may be consecutive, such as, for example, —$CH_2$—NH—$OCH_3$, or —$CH_2$—$CH_2$—S—S—$CH_3$.

A "heterocycloalkyl" ring is a cycloalkyl ring containing at least one heteroatom. A heterocycloalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of non-peroxide O, N(R'), and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, —$CH_2$—CH=CH—$CH_2$—SH, and —CH=CH—O—$CH_2CH_2$—O—$CH_3$.

Aryl groups are ($C_6$-$C_{12}$)cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

The term "heteroaryl" refers to a cyclic aromatic hydrocarbon containing at least one heteroatom, e.g., N, S or non-peroxide O, in the ring. Heteroaralkyl refers to a heteroaromatic ring connected to an alkyl moiety, e.g., pyrid-2-yl methyl.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like.

The invention will be further described by reference to the following detailed examples.

EXAMPLE 1

Preparation of 1-octene from Nonanoic Acid

To a single-necked, 100 mL round-bottom flask equipped with a teflon stirbar is added 20 g nonanoic acid, 22 mg palladium dichloride, 829 mg triphenylphosphine, and 25 mL acetic anhydride, respectively. The flask is equipped with a short-path distillation apparatus with a thermometer, argon balloon, and an attached 100 mL collecting flask in an ice-bath. The reaction flask is heated to a temperature of 230° C. in an oil bath over a 30-40 minute time period, distilling out the excess acetic anhydride, acetic acid byproduct, and olefin product. The reaction is complete after approximately 30 min heating at 230° C. when no more product distills and the solution darkens to a black color due to inactivation of the catalyst. The distillate is then analyzed by NMR to verify the presence of product. The reaction flask is cooled and weighed to determine how much starting material was removed due to reaction (13.5 g, 68% conversion to 1-octene).

EXAMPLE 2

Preparation of cyclohexene from cyclohexane carboxylic acid

To a single-necked, 50 mL round-bottom flask equipped with a teflon stirbar is added 10 g cyclohexane carbpxylic acid, 14 mg palladium dichloride, and 512 mg triphenylphosphine, and 15 mL of acetic anhydride, respectively. The flask is equipped with a short-path distillation apparatus with a thermometer, argon balloon, and an attached 50 mL collecting flask in an ice-bath. The reaction flask is heated to a temperature of 230° C. in an oil bath over a 30-40 minute time period, distilling out the excess acetic anhydride, acetic acid byproduct, and cyclohexene product. The reaction is complete after approximately 30 min heating at 230° C. when no more product distills and the solution darkens to a black color due to inactivation of the catalyst. The distillate is then analyzed by NMR to verify the presence of product. The reaction flask is cooled and weighed to determine how much starting material was removed due to reaction (6.4 g, 64% conversion to cyclohexene).

EXAMPLE 3

Preparation of Methyl Acrylate from Succinic Anhydride

To a single-necked, 100 mL round-bottom flask equipped with a teflon stirbar, is added 20 g succinic anhydride dissolved in 50 mL methanol. The flask is equipped with a reflux condenser topped with a septa and argon balloon, and the reaction mixture is heated to reflux (70° C.) in an oil bath (Dow Corning Fluid) for a 16 hr time period. The reaction flask is then allowed to cool to room temperature, the stirbar removed, and the excess methanol removed via rotary evaporator to give 26.4 g of succinic acid monomethyl ester. In the same 100 mL flask containing succinic acid monomethyl ester is added a teflon stirbar, 35 mg palladium dichloride, 1.31 g triphenylphosphine, and 38 mL acetic anhydride, respectively. The flask is equipped with a short-path distillation apparatus with a thermometer, argon balloon, and an attached 100 mL collecting flask in an ice-bath. The reaction flask is heated to a temperature of 230° C. in an oil bath over a 30-40 minute time period, distilling out the excess acetic anhydride, acetic acid byproduct, and methyl acrylate. The reaction is complete after approximately 30 min heating at 230° C. when no more product distills and the solution darkens to a black color due to inactivation of the catalyst. The distillate is then analyzed by NMR to verify the presence of methyl acrylate. The reaction flask is cooled and weighed to determine how much starting material was removed due to reaction (17.9 g, 68% conversion to methyl acrylate).

EXAMPLE 4

Preparation of Styrene from Hydrocinnamic Acid

To a single-necked, 100 mL round-bottom flask equipped with a teflon stirbar is added 20.1 g hydrocinnamic acid, 25 mg palladium dichloride, and 899 mg triphenylphosphine, and 25 mL of acetic anhydride, respectively. The flask is equipped with a short-path distillation apparatus with a thermometer, argon balloon, and an attached 100 mL collecting flask in an ice-bath. The reaction flask is heated to a temperature of 230° C. in an oil bath over a 30-40 minute time period, distilling out the excess acetic anhydride, acetic acid byproduct, and styrene product. The reaction is complete after approximately 30 min heating at 230° C. when no more product distills and the solution darkens to a black color due to inactivation of the catalyst. The distillate is then analyzed by NMR to verify the presence of styrene. The reaction flask is cooled and weighed to determine how much starting material was removed due to reaction (12.3 g, 61% conversion to styrene).

EXAMPLE 5

Preparation of a Mixture of Alpha-Olefins Under Reduced Pressure

A. To a single-necked, 100 mL round-bottom flask equipped with a teflon stirbar is added 20.72 g myristic acid, 27.23 palmitic acid, and 2.21 g of stearic acid. 45 mg palladium dichloride, and 1.338 mg triphenylphosphine, and 50 mL of acetic anhydride are also added, respectively. The flask is equipped with a short-path distillation apparatus with a thermometer, argon balloon, an attached 100 mL collecting flask in an ice-bath, and placed under vacuum by means of a small vacuum pump (26 torr). The reaction flask is heated to a temperature of 230° C. in an oil bath over a 30-40 minute time period, distilling out the excess acetic anhydride, acetic acid byproduct, and olefin products. The reaction is complete after approximately 30 min heating at 230° C. when no more product distills off and the solution darkens to a black color due to inactivation of the catalyst. The distillate is then analyzed by NMR to verify the presence of products. The reaction flask is cooled and weighed to determine how much starting material was removed due to reaction (36.26 g, 72% conversion to alpha-olefins).

B. A second experiment is run in a 25 mL round-bottom flask using a mixture of 0.42 g myristic acid, 0.56 g palmitic acid, and 0.05 g stearic acid. 2 mg palladium dichloride, 32 mg triphenylphosphine, and 5 mL acetic anhydride are employed in this case. The flask is equipped with a short-path distillation apparatus with a thermometer, argon balloon, an attached 25 mL collecting flask in an ice-bath, and placed under vacuum by means of a small vacuum pump (26 torr). The reaction flask is heated to a temperature of 230° C. in an oil bath over a 30-40 minute time period, distilling out the excess acetic anhydride, acetic acid byproduct, and olefin products. The reaction is complete after approximately 30 min heating at 230° C. when no more product distills and the solution darkens to a black color due to inaction of the catalyst. The distillate is then analyzed by NMR to verify the presence of alkene. The reaction flask is cooled and weighed to determine how much starting material was removed due to reaction (0.77 g, 75% conversion to alpha-olefins).

EXAMPLE 6

Preparation of Alpha-olefins from a Mixture of Fatty Acids from a Biological Sample at Reduced Pressure To a single-necked, 25 mL round-bottom flask equipped with a teflon stirbar is added 0.51 g of a mixture of fatty acids with the following composition: 41.3% of C14, 35.5% of C16:1, 18.8% of C16, and 4.4% of C18. This sample came from the petroleum ether extraction of a fermentate comprising recombinant *E. coli* expressing fatty acids. 5 mg palladium dichloride, 50 mg triphenylphosphine, and 5 mL of acetic anhydride are added to the reaction flask as well. The flask is equipped with a short-path distillation apparatus with a thermometer, an attached 25 mL collecting flask in an ice-bath, and placed under vacuum by means of a small vacuum pump (26 torr). The reaction flask is heated to a temperature of 230° C. in an oil bath over a 30-40 minute time period, distilling out the excess acetic anhydride, acetic acid byproduct, and olefin products. The reaction is complete after approximately 30 min heating at 230° C. when no more products distill and the solution darkens to a black color due to inactivation of the catalyst. The distillate is then analyzed by NMR to verify the presence of alpha-olefins. The reaction flask is cooled and weighed to determine how much starting material was removed due to reaction (0.26 g, 51% conversion to alpha-olefins).

The reaction was repeated under similar reaction conditions (i.e., 26 torr pressure, 230° C. heating) using a sample (3.7 g) of a mixture of fatty acids with the following composition: 34% of C14, 36% of C16:1, 25% of C16, and 5% of C18.6 mg of palladium chloride, 60 mg triphenylphosphine, and 25 mL acetic anhydride were employed in this case. The conversion of this reaction alpha-olefins is 2.1 g (57%).

All patents, patent documents or other publications cited herein are incorporated by reference herein as though fully set forth.

What is claimed is:

1. A method for the decarboxylation of an organic carboxylic acid comprising:
   a) reacting an organic carboxylic acid of the formula (I):

$$R\text{—}CH(Y)\text{—}CH(Z)\text{—}CO_2H \quad (I)$$

wherein R is ($C_8$-$C_{20}$)alkyl or $C_8$-$C_{20}$ alkenyl, Y and Z are H or an organic group, with pivalic anhydride to yield a reaction mixture comprising a mixed anhydride of the formula (II):

$$R^1\text{—}C(O)\text{—}O\text{—}C(O)\text{—}CH(Z)\text{—}CH(Y)\,R \quad (II)$$

wherein $R^1$ is t-butyl;
   b) reacting the mixed anhydride with a catalytic amount of $Pd(PPh_3)_4$, provided by combining $PdCl_2$ with excess $PPh_3$ so that $Pd(PPh_3)_4$ is about 0.01-0.1 mol-% of (I), to yield an intermediate (III) of the formula $$R^1\text{—}C(O)\text{—}O\text{—}Pd(PPh_3)_2\text{—}C(O)\text{—}CH(Z)\text{—}CH(Y)R \quad (III)$$

c) decomposing intermediate (III) to yield a compound of formula $R\text{—}C(Y)\text{=}CH(Z)$ (IV) and $P(Ph_3)_4$, wherein steps (a)-(c) are carried out in the absence of a solvent; and
   d) isolating the compound of formula (IV) from the reaction mixture by distillation at above about 190° C. at less than 1 atm pressure.

2. The method of claim 1 that is carried out at a temperature above about 200° C.

3. The method of claim 1 that is carried out at about 195-250° C.

4. The method of claims 1 wherein the distillation is carried out at about 10-30 Torr.

5. The method of claims 2, 3, 4 or 1 wherein Z and Y are H.

6. The method of claims 2, 3, 4 or 1 wherein the compound of formula (I) is present in a vegetable or animal oil or fat.

* * * * *

UNITED STATES PATENT AND TRADEMARK OFFICE
CERTIFICATE OF CORRECTION

| | | |
|---|---|---|
| PATENT NO. | : 8,629,312 B2 | Page 1 of 1 |
| APPLICATION NO. | : 13/639209 | |
| DATED | : January 14, 2014 | |
| INVENTOR(S) | : George A. Kraus | |

It is certified that error appears in the above-identified patent and that said Letters Patent is hereby corrected as shown below:

In the Specification

In column 1, line 8, before "claims", insert --which--, therefor.

In column 2, line 15, delete "Pd)PPh$_3$)$_2$" and insert --Pd(PPh$_3$)$_2$--, therefor.

In column 9, line 20, delete "carbpxylic" and insert --carboxylic--, therefor.

In the Claims

In column 12, line 7, in claim 1, after "are", insert --individually--, therefor.

In column 12, line 11, in claim 1, delete "CH(Y) R" and insert --CH(Y)R--, therefor.

In column 12, line 18, in claim 1, after "CH", delete "¶", therefor.

In column 12, line 21, in claim 1, delete "CH(Z)(IV)" and insert --C(Z)(IV)--, therefor.

Signed and Sealed this
Twenty-seventh Day of January, 2015

Michelle K. Lee
*Deputy Director of the United States Patent and Trademark Office*